United States Patent
Kuth et al.

(10) Patent No.: US 6,338,836 B1
(45) Date of Patent: Jan. 15, 2002

(54) ASTHMA ANALYSIS METHOD EMPLOYING HYPERPOLARIZED GAS AND MAGNETIC RESONANCE IMAGING

(75) Inventors: Rainer Kuth, Herzogenaurach; Thomas Rupprecht, Uttenreuth, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/406,372

(22) Filed: Sep. 28, 1999

(51) Int. Cl.$^7$ ............................................. A61K 49/00
(52) U.S. Cl. ..................... 424/9.3; 424/9.2; 436/173; 600/410
(58) Field of Search .................. 424/9.2, 9.3; 436/173; 600/410

(56) References Cited

U.S. PATENT DOCUMENTS

| | | | |
|---|---|---|---|
| 5,545,396 A | 8/1996 | Albert et al. | |
| 5,785,953 A | 7/1998 | Albert et al. | |
| 5,789,921 A | 8/1998 | Albert et al. | |

FOREIGN PATENT DOCUMENTS

| | | | |
|---|---|---|---|
| WO | WO 96/40585 | 12/1996 | |
| WO | WO 98/30918 | 7/1998 | |
| WO | WO 99/08766 | 2/1999 | |

OTHER PUBLICATIONS

Okudaira, H. Chest 111:465–515, 1997.*
"Lung Air Spaces: MR Imaging Evaluation with Hyperpolarized $^3$He Gas$^1$" de Lange et al., Radiology, vol. 210 (1999) pp. 851–857.

"Physics of Hyperpolarized Gas NMR in Biomedicine," Darrasse, European Radiology, vol. 9, B2.

"Dynamically Adaptive Hyperpolarized Noble Gas MR Imaging Using Spatially Selective RF Pulse Encoding," Zhao et al., European Radiology, vol. 9, (1999), p. B3, Abstract Only.

"Ultrafast MR–Imaging of Lung Ventilation Using Hyperpolarized Helium–3," Schreiber et al., European Radiology, vol. 9, (1999), p. B28, Abstract Only.

* cited by examiner

*Primary Examiner*—Patrick J. Nolan
*Assistant Examiner*—Gerald R. Ewoldt
(74) *Attorney, Agent, or Firm*—Schiff Hardin & Wait

(57) ABSTRACT

In an integrated asthma analysis and therapy determination method, a patient is administered hyperpolarized gas and an magnetic resonance (MR) scan is conducted to obtain a first MR image set, and the patient is then administered an allergen provoker and is again administered hyperpolarized gas and another MR scan is conducted, to obtain a second MR image set. This is followed by administering asthma therapeutics and again administering hyperpolarized gas to the subject, and another MR scan is conducted to obtain a third image data set. The first, second and third image data sets are compared among each other in order to determine the effect of the allergen provoker and the effect of the asthma therapeutics, in order to determine an appropriate medication dosage for the subject.

7 Claims, 1 Drawing Sheet

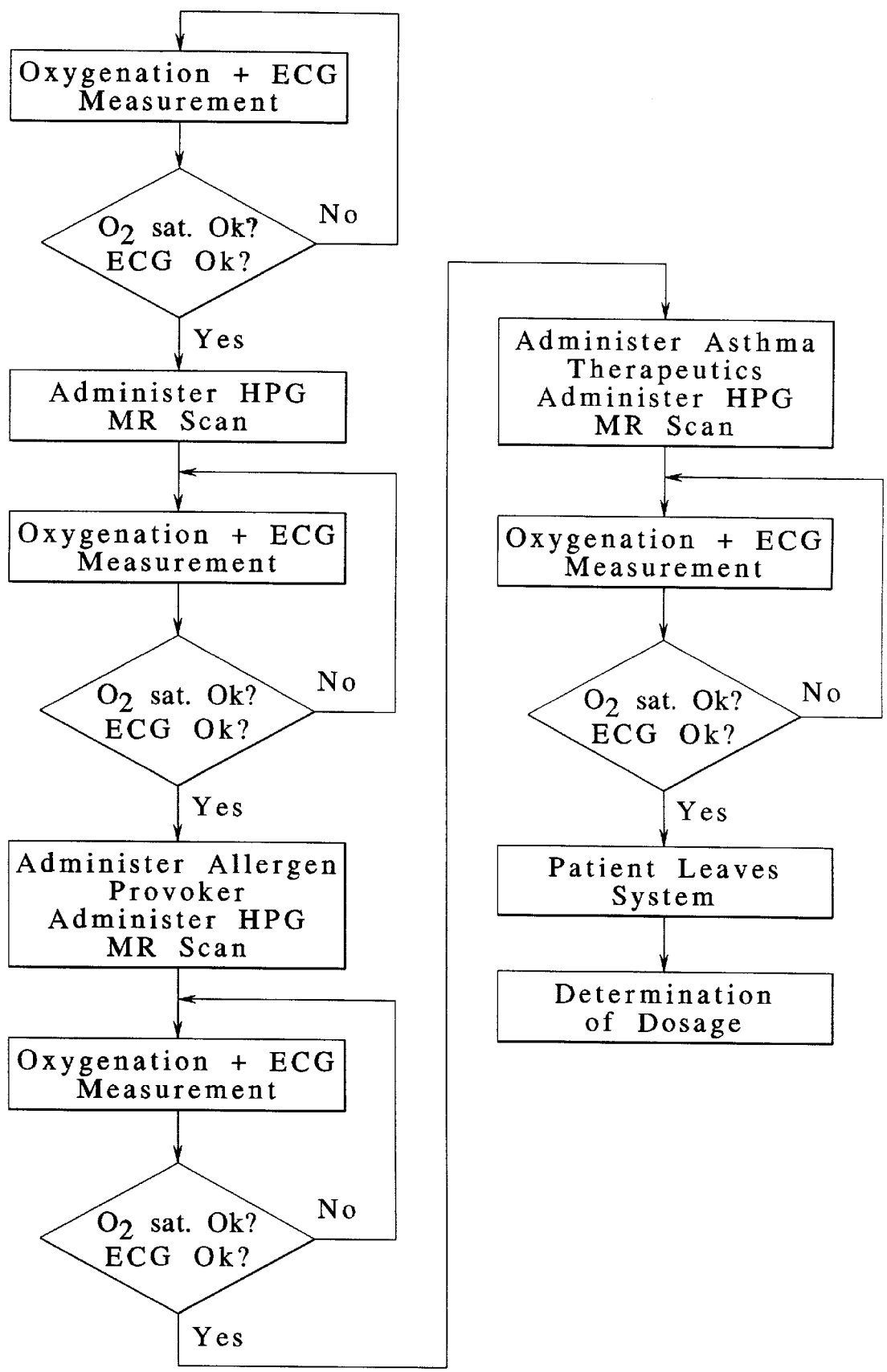

ASTHMA ANALYSIS METHOD EMPLOYING HYPERPOLARIZED GAS AND MAGNETIC RESONANCE IMAGING

BACKGROUND OF THE INVENTION

1. Field of the Invention

The present invention is directed to a procedure which combines asthma analysis and therapy in the context of magnetic resonance scanning of a subject.

2. Description of the Prior Art

Asthma is a serious illness of the lungs characterized by recurring attacks of dyspnea (shortness of breath), a feeling of pressure on the chest, wheezing, cough, fear, etc. The distressing symptoms are caused by a constriction of the bronchial tubes, which are the tube-like structures that carry air to and from the lungs. The length of an asthma attack can vary; it may last for a few minutes or several hours, or longer.

The primary cause of so-called "true" asthma is sensitivity to certain substances, generically referred to as allergens.

There are approximately 100 million asthmatics worldwide. Asthma is one of the most common causes of death of persons under 50 years of age in highly developed countries, wherein instances of this illness continuously increase. Although several types of medication are available for asthma therapy, each type of medication is effective only for specific groups of patients. Other than the triggering effect of an allergen, the mechanism which produces an asthma attack is still not completely understood, particularly on an individual patient basis. Because of this lack of knowledge, it is extremely difficult, if not impossible, to find an optimal dosage for the medication. The patient himself or herself is not aware of the presence of the latent illness before a dangerous condition already has been reached, typically the occurrence of an attack. Under normal circumstances, an asthmatic feels comfortable during times when the illness is latent, but begins to experience repeated and surprising asthma attacks, which can be very dangerous. The separation in time, and the seeming spontaneity, of such asthma attacks compound the problem of prescribing an appropriate dosage of therapeutic medication.

The following examination techniques and dosage prescriptions are currently practiced in the field of asthma therapy.

A thorax X-ray is a fast and inexpensive examination technique, but has a highly limited informational content, because the thorax X-ray image only represents a two-dimensional projection of the lung onto the X-ray film, and shows very little soft tissue contrast.

Computed tomography is a relatively expensive method and requires longer measuring time and exposes the patient to a dose of ionizing radiation. Computed tomography is therefore not practical for patients requiring repeated examinations, particularly young patients.

Lung function measurements, such as those obtained by connecting a patient to a ventilator, are relatively inexpensive and allow conclusions to be made regarding the functioning of a patient's lungs with a specific time resolution. Such lung function measurements, however, provide no visual information of the lungs themselves.

As a supplement to lung function measurements, an allergen provoker can be administered to the patient so that changes in the functioning of the patient's lungs as a result of the presence of the allergen can be monitored and analyzed.

Scintigraphy (i.e., imaging using a scintillation camera) provides spatially resolved functional information, but the spatial resolution is relatively modest and can be conducted only by personnel trained in nuclear medicine.

The production and properties of hyperpolarized gases are well known and are described, for example, in PCT Application WO 99/08766. Obtaining magnetic resonance images after administering a hyperpolarized gas to a patient is a known technique for monitoring physiological processes because the hyperpolarized gas produces a uniquely identifiable magnetic resonance (MR) signal, and thus the diffusion of the hyperpolarized gas into body tissue and organs can be monitored in one or more MR images. The use of this technique for lung imaging and analysis is described in the article "Kernspintomographie der Lunge mit hochpolarisiertem Helium-3," Schreiber et al., Physilkalische Blätter 55, No. 3 (1999) pages 45–47. $^3$He or $^{129}$Xe is polarized up to approximately 60 percent by spin exchange under laser irradiation. This hyperpolarized gas (HPG) is administered to the patient for one breath. During the inhalation and the subsequent phase wherein the air is held, a series of MR images of the patient is obtained. The measuring time is determined by the subsidence of the hyperpolarization in the lung, and by the time that the patient holds his or her breath. The hyperpolarization subsides primarily due to reaction with $O_2$ (see "Physics of Hyperpolarized Gas NMR in Biomedicine," Darrasse, European Radiology 9, Abstracts B2 (1999)) and the flip angle of the MR sequence (see "Dynamically Adaptive Hyperpolarized Noble Gas MR Imaging Using Spatially Selective RF Pulse Encoding," Zhao et al., European Radiology 9, Abstracts B3 (1999)).

Only the polarized noble gas is visible in the MR images, thereby providing information regarding ventilation of the lung with a high degree of spatial resolution. The results of different MR measuring sequences are described in the article "Lung Air Spaces:MR Imaging Evaluation With Hyperpolarized $^3$He Gas," de Lange et al., Radiology, Volume 210, No. 3, pages 851–857 (March 1999). Depending on the measuring sequence, one or several images of the ventilated areas of the lung, in one or several slices can be acquired. Alternatively, a time history of the ventilation can be acquired, but with a relatively low spatial resolution, as described in "Ultrafast MR Imaging of Lung Ventilation Using Hyperpolarized Helium-3," Schreiber et al., European Radiology 9, Abstracts B28 (1999).

Subsequently, breathing air, possibly enriched with oxygen, is administered to the patient and after a waiting period, when it is assured that the patient's blood oxygenation is normal, the examination can be repeated or the patient can be discharged.

SUMMARY OF THE INVENTION

It is an object of the present invention to provide a combined procedure for asthma analysis and therapy determination which does not expose a patient to ionizing radiation and which provides high time resolution and spatial resolution.

The above object is achieved in accordance with the principles of the present invention and integrated asthma analysis and therapy determination method wherein hyperpolarized gas is administered to a patient in a "normal" state, i.e. the patient is not exhibiting acute asthmatic symptoms, and an MR scan of the patient's lungs is undertaken, to obtain a first MR image or a first MR image sequence. Subsequently, an allergen provoker is administered to the patient, hyperpolarized gas is again administered to the patient, and a further MR scan of the patient's lungs is conducted, so as to obtain a second MR image or a second series of MR images. Subsequently, asthma therapeutics, such as medication, are administered to the subject, hyperpolarized gas is again administered to the subject, and another MR scan of the patient's lungs is conducted, to obtain a third MR image or a third series of MR images. The patient then leaves the MR system. The first, second and third images or the first, second and third series of images are then compared with each other so as to obtain an indication of the difference between the state of a patient's lungs in the "normal" condition and in the condition after allergen provocation, and in the condition after asthma therapy has been administered. The physiological affect of the presence of the allergen can be ascertained by comparing the first and second images, or first and second series of images, and the effectiveness of the administered asthma therapy can be ascertained not only by comparing the second and third images, or second and third series of images, but also by comparing the first and third images, or the first and third series of images.

After each MR scan, the patient's blood oxygenation can be measured and/or an electrocardiogram (ECG) can be obtained from the patient, in order to insure that the patient is not adversely affected by the procedure. Such a blood oxygenation measurement and/or an ECG also can be obtained prior to conducting the first MR scan, in order to provide baseline data.

DESCRIPTION OF THE DRAWING

The single FIGURE is a flowchart of an integrated asthma analysis and therapy determination, in accordance with the present invention.

DESCRIPTION OF THE PREFERRED EMBODIMENTS

In the integrated asthma analysis and therapy determination method in accordance with the invention, the basic steps of administering hyperpolarized gas and conducting an MR scan, administering an allergy-provoking agent and conducting a further MR scan, and administering asthma therapeutics and conducting another MR scan are combined in an integrated procedure. The MR scanning of a patient to whom hyperpolarized gas has been administered provides time resolved and spatially resolved functional information without and with the influence of allergy-provoking agents and/or asthma therapeutics. These images are compared with images of the patient in a "normal" state and the functioning of the lungs is thereby analyzed, by means of the images, in a spatially resolved and time resolved manner so that the effects of the allergy-provoking agent and/or the asthma therapeutics can be determined.

The allergy (or allergen) provoking agents can be administered in a concentrated manner and their localized effect can be examined, and most likely their effect will not be perceived by, or at least will not produce significant discomfort to, the patient. Moreover, the internal effect of such allergen-provoking agents would not be recognizable in conventional procedures such as scintography.

Moreover, since the procedure does not expose the patient to ionizing radiation, it can be repeated relatively often to monitor or update the therapy determination and to determine whether the patient's asthmatic condition has changed. Because the patient is not exposed to ionizing radiation, the normal "tradeoff" of deciding whether the analysis result is sufficiently beneficial so as to justify the radiation exposure will almost always be in favor of conducting the examination according to the inventive procedure. Therefore, the procedure is suitable not just for examining persons who already exhibit asthma symptoms, but also for examining persons who may be candidates for developing the disease in acute form in the future. Thus, persons who are relatives of asthmatics or who may acquire asthmatic symptoms as a result of particular jobs which entail an exposure to different types of allergens, can be examined using the inventive procedure. This can be useful, for example, for screening job candidates and/or for monitoring persons working at a particular job to identify asthmatic conditions if and when they arise.

Moreover, because of the spatial resolution and time resolution which is obtained with the aforementioned images, a higher degree of specificity and reliability in the determination of the medication dosage can be made, and the effectiveness over time can be monitored more easily.

Additionally, the images and/or the diagnostic conclusions can be maintained in an accumulating database, so that geographic, work-related and other trends can be tracked. As set forth in the flowchart, when a patient first begins the procedure, the patient's blood oxygenation and ECG can be obtained, and if any abnormalities are identified, the remainder of the procedure can be delayed until these abnormalities subside, or if it is likely that the abnormalities will not quickly subside, the patient can be asked to return at another time. Additionally, these initial measurements provide a baseline for subsequent measurements.

A hyperpolarized gas, such as $^3$He, is then administered to the patient and an MR scan is conducted. One or more images of the patient's lungs are obtained in this first scan, the images being obtained according to any suitable known manner of the type initially described.

Subsequently, an allergen provoker is administered to the patient, hyperpolarized gas is also again administered to the patient, and a second MR scan is conducted, resulting in a further MR image or series of MR images showing the effect of the allergen provoker.

Subsequently, asthma therapeutics, such as medication, are administered to the patient, hyperpolarized gas is again administered to the patient, and a third MR scan is conducted, to obtain another MR image or series of MR images.

As shown in the flowchart, after each MR scan, the patient's blood oxygenation and ECG are monitored. This is desirable and recommended for the safety of the patient, however, it is not crucial to obtaining the three different sets of MR images in accordance with the invention.

After the last of the MR scans, the patient can be once again checked as to blood oxygen saturation and ECG, and discharged. At that time, or subsequently, the first, second and third sets of MR images can be compared so that an appropriate medication dosage can be prescribed. The first and second sets of MR images are compared to determine the effect of the allergen provoker on the patient's lungs, and the effect of the administered asthma therapy can be ascertained by comparing the second and third sets of images, possibly augmented by comparing the first and third sets of images as well.

As used herein, the term "set of images" can include only a single image.

Although modifications and changes may be suggested by those skilled in the art, it is the intention of the inventor to embody within the patent awarded hereon all changes and modifications as reasonably and properly come within the scope of his contribution to the art.

We claim:

1. A method for determining effectiveness of an asthma therapy, comprising the steps of, in a continuous procedure:

(a) administering hyperpolarized gas to a subject and conducting a magnetic resonance thorax scan of the subject to obtain a first image set which indicates a degree of diffusion of said hyperpolarized gas in the subject's lungs;

(b) administering an allergen provoker to the subject at a level that is not recognizable in a scintographic image and administering hyperpolarized gas to the subject and conducting a second magnetic resonance thorax scan of the subject to obtain a second image set which indicates a degree of diffusion of said hyperpolarized gas in the subject's lungs;

(c) administering asthma therapy to the subject and administering hyperpolarized gas to the subject and conducting a third magnetic resonance thorax scan of the subject to obtain a third image set which indicates a degree of diffusion of said hyperpolarized gas in the subject lungs; and (d) comparing said first image set, said second image set and said third image set among each other, using said first image set as a baseline, and determining a difference between the respective degrees of diffusion of said hyperpolarized gas in said second and third image sets, and evaluating an effectiveness of said asthma therapy therefrom.

2. A method as claimed in claim 1 comprising, at preceding step (a), obtaining at least one of a blood oxygenation measurement and an electrocardiogram from said subject.

3. A method as claimed in claim 1 comprising, after step (a), obtaining at least one of a blood oxygenation measurement and an electrocardiogram from said subject.

4. A method as claimed in claim 1 comprising, after step (b), obtaining at least one of a blood oxygenation measurement and an electrocardiogram from said subject.

5. A method as claimed in claim 1 comprising, after step (c), obtaining at :east one of a blood oxygenation measurement and an electrocardiogram from said subject.

6. A method as claimed in claim 1 comprising, after each of steps (a), (b) and (c), obtaining at least one of a blood oxygenation measurement and an electrocardiogram from said subject.

7. A method as claimed in claim 1 comprising, preceding step (a) and after each of steps (a), (b) and (c), obtaining at least one of a blood oxygenation measurement and an electrocardiogram from said subject.

* * * * *